United States Patent
Xu et al.

(10) Patent No.: US 10,328,154 B2
(45) Date of Patent: Jun. 25, 2019

(54) TOPICAL COMPOSITIONS FOR IMPROVED DELIVERY OF ACTIVE AGENTS

(71) Applicant: BUFFERAD Illinois Inc., Lake Bluff, IL (US)

(72) Inventors: Xiaoyan Xu, Long Grove, IL (US); Wen Yang, Evanston, IL (US); Nguyet Le, Lake Forest, IL (US); Jerry Z. Zhang, Long Grove, IL (US)

(73) Assignee: BUFFERAD Illinois Inc., Lake Bluff, IL (US)

( * ) Notice: Subject to any disclaimer, the term of this patent is extended or adjusted under 35 U.S.C. 154(b) by 103 days.

(21) Appl. No.: 15/796,517

(22) Filed: Oct. 27, 2017

(65) Prior Publication Data

US 2019/0125880 A1    May 2, 2019

(51) Int. Cl.

| | |
|---|---|
| *A61K 47/06* | (2006.01) |
| *A61K 47/34* | (2017.01) |
| *A61K 47/12* | (2006.01) |
| *A61K 47/44* | (2017.01) |
| *A61K 47/10* | (2017.01) |
| *A61K 9/00* | (2006.01) |
| *A61K 47/32* | (2006.01) |

(52) U.S. Cl.
CPC ............ *A61K 47/44* (2013.01); *A61K 9/0014* (2013.01); *A61K 47/06* (2013.01); *A61K 47/10* (2013.01); *A61K 47/12* (2013.01); *A61K 47/32* (2013.01); *A61K 47/34* (2013.01)

(58) Field of Classification Search
CPC ......... A61K 47/06; A61K 47/34; A61K 47/12
USPC ............................ 514/772, 772.5, 772.7, 784
See application file for complete search history.

(56) References Cited

U.S. PATENT DOCUMENTS

| | | | |
|---|---|---|---|
| 3,574,827 A * | 4/1971 | Beerbower .......... | A61K 8/8111 514/762 |
| 4,983,385 A * | 1/1991 | Hasegawa .............. | A61K 9/006 514/772.4 |
| 5,244,673 A * | 9/1993 | Gejkova ............... | A61K 9/0048 424/486 |
| 2005/0250805 A1* | 11/2005 | Kannan ................ | A61K 9/0014 514/291 |

\* cited by examiner

*Primary Examiner* — Raymond J Henley, III
(74) *Attorney, Agent, or Firm* — Beem Patent Law Firm

(57) ABSTRACT

A topical composition and methods of making the composition is disclosed. The composition may comprise an ointment base, C11-C40 alcohols or acids, and a polymer. The ointment base may be in an amount of at least about 50% of the topical composition by weight. The polymer may be substantially soluble in the ointment base.

23 Claims, No Drawings

TOPICAL COMPOSITIONS FOR IMPROVED DELIVERY OF ACTIVE AGENTS

FIELD

This disclosure relates to a topical pharmaceutical composition and method of making thereof, particularly, to an improved release of active agents from an ointment base, such as petrolatum based compositions comprising said agents and release enhancing agents.

BACKGROUND

The administration of drugs and other biological materials to the bloodstream via a transdermal route or to the localized site of action has received much attention in recent years. The skin of an average adult covers generally more than two square meters of surface area and receives about one third of all blood circulating through the body. It is elastic, rugged, and generally self-generating. The skin consists of three layers: the stratum corneum, the epidermis, and the dermis.

The stratum corneum represents the rate limiting step in diffusion of chemicals through the skin. The stratum corneum is composed of dead, keratinized, metabolically inactive cells, which are closely packed together, and consists of an amorphous matrix of mainly lipoid and non fibrous protein within which keratin filaments are distributed. The cells of the stratum corneum generally contain about 20% water, while the cells below, in the stratum germinivatum contain about 70% water. The stratum corneum does not become hydrated readily. Thus, transdermal permeation is primarily controlled by diffusion through the stratum corneum.

Due to availability of large surface area, easy accessibility, application dynamics and the noninvasive nature of the therapy, topical administration of drugs has long been considered a promising route of drug delivery whether the bioavailability desired is systemic, dermal, regional or localized. The topical mode of drug delivery provides many advantages over customarily used routes of administration. First, it bypasses the portal circulation and thereby the hepatic first pass metabolism. Second, topical delivery avoids the problems of variable systemic absorption and metabolism. Third, it potentially reduces gastrointestinal irritation associated with oral administration. Further, it avoids the risks and patient noncompliance associated with parenteral treatment.

The topical delivery route offers continuity of drug administration, permits use of therapeutic agents with short biological half-lives, provides treatment of cutaneous manifestations of diseases usually treated systemically, delivers medication directly into the systemic circulation, and fosters ease of use and total patient compliance.

Ointments are semisolid preparations intended for external application to the skin or mucous membranes. Ointments may be medicated or non-medicated. Non-medicated ointments are ordinarily used for the physical effects that they provide as protectants, emollients or lubricants. Medicated ointments include an active pharmaceutical ingredient (API). Ointments include an ointment base component, such as petrolatum.

Petrolatum based topical compositions possess occlusive and emollient properties and are often used in for the delivery of active agents. However, because of the viscous and lipophilic nature of petrolatum, the release of active agents from petrolatum based compositions is generally slow and can hinder therapeutic efficacy. Slow delivery can be a particular problem when the composition includes an active agent that is water-miscible or hydrophilic. For example, petrolatum based compositions are desirable for treatment of bacterial, fungal infection, and wound healing applications where an occlusive layer formed by petrolatum is highly desirable. However, many agents that have anti-bacterial, anti-fungal, and wound-healing activities are water-miscible or hydrophilic and may not release efficiently through the petrolatum. Efficacies of the dosage forms are believed to be directly related to amount of the active agents being released from the dosage forms to targeted tissues, such as, for example, skin, ocular, or nasal tissues. Release of the active agents from the petrolatum based compositions is thought to be through diffusion of the agents from within the compositions to surface of the compositions. For compositions intended to treat bacterial, fungal infection, or for wound healing, enhanced release of the active agents generally corresponds to enhanced therapeutic efficacy. In addition, enhanced release of the active agents might also lead to enhanced delivery to various animal or human tissues, such as, skin, ocular, nasal, for example, when the compositions are applied topically to surfaces of the tissues.

There is a need for release enhancing agents to increase release of active agents from petrolatum based compositions. There is also a need for topical compositions with enhanced therapeutic efficacy.

SUMMARY

In one embodiment, a topical composition may comprise an ointment base, C11-C40 alcohols or C11-C40 acids, or combinations thereof, and a polymer. The ointment base may be in an amount of at least about 50% of the topical composition by weight. The polymer may be substantially soluble in the ointment base.

In another embodiment, a topical composition may comprise (a) a therapeutically effective amount of an active agent; (b) a petrolatum ointment base; (c) C11-C40 alcohols or acids, or combinations thereof; and (d) substantially soluble polymer in the petrolatum ointment base. A combination of alcohols or acids with the polymer may enhance a release of the active agent.

In further another embodiment, a process for preparing an ointment composition may be carried out by dissolving or suspending a therapeutically effective amount of an active ingredient in an ointment base. The process may further be carried out by mixing C11-C40 alcohols or C11-C40 acids, or combinations thereof and mixing a polymer. The polymer may be substantially soluble in an ointment base.

Additional features and advantages of the present disclosure will be set forth in the detailed description, which follows, and in part will be readily apparent to those skilled in the art from that description or recognized by practicing the embodiments described herein, including the detailed description, which follows, the claims, and the appended drawings.

It is to be understood that both the foregoing general description and the following detailed description describe various embodiments and are intended to provide an overview or framework for understanding the nature and character of the claimed subject matter.

DETAILED DESCRIPTION

The present disclosure can be understood more readily by reference to the following detailed description, examples, and claims, and their previous and following description.

However, before the present compositions, articles, devices, and methods are disclosed and described, it is to be understood that this disclosure is not limited to the specific compositions, articles, devices, and methods disclosed unless otherwise specified, as such can, of course, vary. It is also to be understood that the terminology used herein is for the purpose of describing particular aspects only and is not intended to be limiting.

Definitions

"Polymer", as used herein, includes homopolymers or copolymers.

"Co-polymer", as used herein, refers to any polymer composed of two or more different monomers.

The term "therapeutically effective amount" as used herein means the amount of a compound that, when administered to a subject for treating a state, disorder or condition, is sufficient to effect such treatment. The "therapeutically effective amount" will vary depending on the compound, the disease, its severity, the age, weight, physical condition and responsiveness of the subject to be treated.

The term "delivering" as used herein means providing a therapeutically effective amount of an active ingredient to a particular location within a host means causing a therapeutically effective blood concentration of the active ingredient at the particular location. This can be accomplished, e.g., by topical, local or by systemic administration of the active ingredient to the host.

The term "subject" or "a patient" or "a host" as used herein refers to mammalian animals, preferably human.

As used herein, the term 'about' will be understood by persons of ordinary skill in the art and will vary to some extent on the context in which is used. If there are uses of the term which are not clear to persons of ordinary skill in the art given the context in which is used, 'about' may mean up to plus or minus 20% of the particular term.

"Penetration enhancement" or "permeation enhancement" as used herein relates to an increase in the permeability of the skin or mucosal tissue to the selected pharmacologically active agent, which in turn gives rise to an increase in the rate at which the drug permeates into and/or through the skin or mucosal tissue. Exemplary penetration enhancers include, by way of example and without limitation, volatile organic solvents (e.g. alcohols such as ethanol), nonvolatile organic solvents (e.g. amides such as pyrrolidones; polyol ethers such as glycol ethers; polyols such as glycols; and derivatives thereof) and the like and mixtures thereof.

A "skin penetration enhancer", as used herein, is a pharmaceutically acceptable chemical compound or a suitable combination of such compounds that when present in a composition, enhances skin absorption and penetration of a second chemical compound, such as an active agent, in the composition. It is known in the art that certain chemical compounds possess properties of skin penetration enhancement. Examples include but not limited to: pyrrolidones such as, 2-pyrrolidone, N-methyl 2-pyrrolidone; ethylene glycol monoalkyl ether (e.g., monomethyl, monoethyl, monopropyl, monobutyl, monopentyl, monohexyl, monophenyl), ceramides, sphigomyelins; surfactants such as for example, sodium laureth sulfate, sodium lauryl sulfate, sorbitan monooleate, sorbitan monolaurate, glyceryl monostearate, glyceryl monolaurate, glyceryl monooleate, terpenes, azone, menthol, camphor, etc.

The terms "active", "drug", and "active pharmaceutical ingredient" are used interchangeably herein.

The term "ointment" for use herein may be any commonly known and commercially available ointments.

Broadly, the embodiments relate to a topical pharmaceutical composition and method of making thereof. The topical pharmaceutical composition, such as petrolatum based compositions, often also referred to as oleaginous ointment, is commonly used topical dosage form for delivery of active agents for cosmetic or therapeutic applications.

It has been unexpectedly discovered that release of active agents from petrolatum based compositions is enhanced by using a synergistic mixture of release enhancing agents, comprising a polymer that is soluble in the compositions and a terminally functionalized hydrocarbons having about 11 to about 40 carbon atoms wherein the functional group is an alcohol or carboxylic acid.

In one aspect, a topical composition may comprise an ointment base, C11-C40 alcohols or C11-C40 acids, such as carboxylic acids, and a polymer. The ointment base may be at least about 50% of the topical composition by weight. The polymer may be substantially soluble in the ointment base.

In some embodiments, the topical composition can further comprise an active agent. In other embodiments, the topical composition can comprise a penetration enhancer.

As one skilled in the art will readily appreciate, the specific ointment base to be used is one that will provide for optimum drug delivery, and, preferably, will provide for other desired characteristics as well, e.g., emolliency and occluded-ness. As with other carriers or vehicles, an ointment base should ordinarily be inert, stable, nonirritating and nonsensitizing. Generally, the ointment base may be grouped in four classes: oleaginous bases; emulsifiable bases; emulsion bases; and water-soluble bases. See, e.g., *Remington: The Science and Practice of Pharmacy*, 19th Ed. (Easton, Pa.: Mack Publishing Co., pp. 1301-1306 (1985). Oleaginous ointment bases include, for example, vegetable oils, synthetic oleaginous esters of carboxylic acids and alcohols, fats obtained from animals, semisolid hydrocarbons obtained from petroleum and the like.

Examples of oleaginous ointment bases include white ointment, yellow ointment, cetyl esters wax, paraffins, petrolatum, white petrolatum, white wax, yellow wax, beeswax, and the like and mixtures thereof. Emulsifiable ointment bases, also known as absorbent ointment bases, contain little or no water and include, for example, hydroxystearic sulfate, anhydrous lanolin, hydrophilic petrolatum and the like and mixtures thereof. Emulsion ointment bases are either water-in-oil (W/O) emulsions, or oil-in-water (O/W) emulsions, and can include, for example, cetyl alcohol, lanolin, glyceryl monostearate, stearic acid and the like and mixtures thereof. Useful water-soluble ointment bases can be those prepared from glycol ethers such as, for example, polyethylene glycols of varying molecular weight, polysorbates and the like and mixtures thereof. Petrolatum may be at a concentration of greater than or equal to 50%, preferably greater than or equal to 70%, for example.

In some embodiments of this aspect, the C11-C40 alcohol or the C11-C40 carboxylic acid, or combinations thereof may be present in an amount of about 0.1% to about 20%, preferably 0.1 to 15%, more preferably 0.1 to 10%, for example, of the composition by weight. In certain embodiments, the C11-C40 alcohol may be a terminally functionalized alkyl alcohol having 11 to 40 carbon atoms, preferably having 16 to 40 carbon atoms, more preferably 20 to 40 carbon atoms, for example.

The general formula of the terminally functionalized alkyl alcohols are: $R_n(OH)$, wherein n is equal to or greater than 11 and equal to or less than 40; wherein R is a saturated or unsaturated hydrocarbon chain. Examples of saturated and unsaturated alkyl alcohols suitable for preparing the compositions of the present embodiment are 1-dodecanol, 1-tridecanol, 1-tetradecanol, 1-pentadecanol, 1-hexadecanol, 1-heptadecanol, 1-octadecanol, 1-nonadecanol, 1-eicosanol, 1-heneicosanol, 1-docosanol, 1-tetracosanol, 1-hexacosanol, 1-heptacosanol, 1-octacosanol, 1-nonacosanol, 1-triacontanol, 1-dotriacontanol, 1-tetratriacontanol, tridecyl alcohol, palmitoleyl alcohol, erucyl alcohol, and combinations thereof. Lanolin alcohol is also suitable.

In certain embodiments, the C11-C40 acids may be terminally functionalized alkyl carboxylic acids having a general formula: Rn(COOH), wherein n is equal to or greater than 11 and equal to or less than 40. In one embodiment, R may be a saturated or unsaturated hydrocarbon chain.

Examples of saturated carboxylic acids suitable for preparing the compositions of the present embodiment are lauric acid, tridecylic acid, myristic acid, pentadecyclic acid, palmitic acid, margaric acid, stearic acid, nonadecyclic acid, arachidic acid, heneicosylic acid, benenic acid, tricosylic acid, lignoceric acid, pentacosylic acid, cerotic acid, heptacosylic acid, montanic acid, nonacosylic acid, melissic acid, henatriacontylic acid, lacceroic acid, psyllic acid, geddic acid, ceroplastic acid, hexatriacontylic acid, heptatriacontanoic acid, octatriacontanoic acid, and combinations thereof.

Examples of unsaturated carboxylic acids suitable for preparing the compositions of the present embodiment are myristoleic acid, palmitoleic acid, α-linolenic acid, linoleic acid, stearidonic acid, γ-linolenic acid, vaccenic acid, oleic acid, elaidic acid, sapienic acid, eicosapentaenoic acid, dihomo-γ-linolenic acid, arachidonic acid, paullinic acid, gondoic acid, erucic acid, docosahexaenoic acid, docosatetraenoic acid, linoelaidic acid, eicosapentaenoic acid, nervonic acid, sardine acid, herring acid, mead acid, and combinations thereof.

Salts of the unsaturated and saturated carboxylic acids are also suitable for preparing the compositions of the present embodiment. Examples include sodium stearate, magnesium stearate, sodium behenate, sodium oleate, calcium oleate, magnesium oleate, sodium linoleate, and combinations thereof.

The polymer in the compositions may be at a concentration of about 0.1% to about 20%, preferably about 0.1 to about 15%, more preferably about 0.1 to about 10%.

The polymer might be poly α-olefins, polyaromatics, or fluoropolymers. Examples of poly α-olefins include polyethylene, polypropylene, polybutylene, poly-1-hexadecene, and poly-1-eicosene. Examples of polyaromatics include polystyrene, substituted polystyrene. Examples of fluoropolymers include polyvinylidene fluoride, polyvinyl fluoride.

The polymer might also be a copolymer. Examples of monomers in the copolymer include vinyl monomers, styrene and functionalized styrene monomers, and α-olefins. In one embodiment, the olefin may comprise α-olefins having at least 11 carbon atoms. It is believed that a copolymer comprising different monomer units is generally preferred for its ability to loosen and disrupt dense and orderly packing of hydrocarbons in petrolatum than a polymer comprising only same monomer units. Furthermore, a copolymer with different monomer units might help dispersion and solubilization of the active agents. Therefore, a copolymer is preferred.

Examples of vinyl monomers include vinyl acetate, maleic acid, and vinyl pyrrolidone. A copolymer of vinyl monomers and α-olefins is preferred. According to the present embodiment, the copolymer needs to be solubilized in the composition base comprising petrolatum. Hydrophobicity of α-olefins increases as the chain length increases. Due to highly hydrophobic nature of the petrolatum base, long chain α-olefins are believed to make the copolymer more soluble in the composition comprising petrolatum. Therefore, copolymers of vinyl monomers and long chain α-olefins are preferred. The long chain α-olefins may have at least 11 carbon atoms, preferably at least 16 carbon atoms, more preferably at least 20 carbon atoms.

Because of the occlusive, emollient, and non-irritating properties of petrolatum, it is desirable to maintain these desirable properties. Therefore, the release enhancing agents, such as alcohols, acids or polymers may be present in an amount of about 0.1 to about 20%, preferably about 0.1 to about 15%, more preferably about 0.1 to about 10%, more preferably about 0.1% to about 5%.

Combinations of terminally functionalized alkyl alcohols and carboxylic acids in any given ratio are also suitable for preparing the compositions of the present embodiment.

The active agent may be any suitable chemical or biological compound. The active agent may be a cosmetically or pharmacologically active agent.

All physical forms of a given active agent, crystalline, semi-crystalline, and amorphous, are contemplated and within the scope of the present embodiment, either in admixture or in pure or substantially pure form. Furthermore, the stereoisomers of a given active agent are also contemplated and within the scope of the present embodiment. The definition of a given active agent in accordance with the present embodiment embraces all possible stereoisomers and their mixtures. It particularly embraces the racemic forms and the isolated optical isomers having the specified activity.

The active agent may be selected from a group consisting of analgesic agents, anesthetic agents, anti-microbial agents, anti-viral agents, cardio agents, estrogen agents, retinoid agents, immunosuppressive agents, corticosteroid agents, non-steroidal anti-inflammatory drugs (NSAIDs), proteins, enzymes, hair-growth agents, ophthalmic agents, dermatological agents, cosmetic agents, moisturizing agents, urea or allantoin, antifungal agents, anti-bacterial agents, and wound-healing agents.

Anti-microbial agents may include erythromycin, clindamycin, bacitracin, tobramycin, neomycin, neosporin, polymycin B, benzoyl peroxide, mupirocin, cephalosporins, and penicillins, gentamicin, tetracyclines, streptomycin, kanamycin, vanomycin, rifampin, minocycline, doxycycline, lincomycin, temflaxocine, ciproflaxocine, levoflaxocine, gatiflaxocine, quinolones, fluoroquinolones, sulfonamides, aminoglycosides, for example.

Anti-fungal agents may include bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, efinaconazole, epoxiconazole, fluconazole, isavuconazole, itraconazole, posaconazole, propiconazole, ravuconazole, terconazole, voriconazole, abafungin, amorolfin, butenafine, naftifine, terbinafine, ciclopirox, flucytosine, griseofulvin, tolnaftate, amphotericin B, candicidin, filipin, hamycin, natamycin, nystatin, rimocidin, anidulafungin, caspofungin, micafungin, crystal violet, for example.

Anti-viral agents may include abacavir, acyclovir, arbidine, cidofovir, doluregravir, edoxudine, famciclovir, ganciclovir, oseltamivir, valaciclovir, for example. Cardioactive agents may include organic nitrates such as nitroglycerine, isosorbide dinitrate, and isosorbide mononitrates; quinidine sulfate; procainamide; thiazides such as chlorothiazide, and hydrochlorothiazide; nifendipine, nicardipine, adrenergic blockers, such as timolol, propranolol, verapamil, dithiazem, captopril, and clonidine, for example.

Estrogens may include conjugated estrogens, esterified estrogens, 17-β-estradiol, 17-β-estradiol valerate, mestranol, estriol, or any estrogen or its derivatives suitable for use in hormone replacement therapy, for example.

Retinoids, keratolytic drugs and related to retinoic acid, may generally include chemical entities such as retinol and its esters and closely related naturally-occurring derivatives and structurally-related synthetic analogs. This includes, for example, retinol, retinal, tretinoin (all-trans retinoic acid), isotretinoin, adapalene (6-[3-(1-adamantyl)-4-methoxyphenyl]-2-naphthoic acid), Tazarotene, and the like, for example.

Analgesics and anesthetics may include lidocaine, tetracaine, dibucaine, prilocaine, benzocaine, capsaicin, fentanyl, pregabalin, gabapentin, carbamazepine, oxcarbazepine, duloxetine, venlafaxine, bupropion, and opioids, for example. Immunosuppressive agents may include methatrexate, cyclosporins, tacrolimus, pimecrolimus, sirolimus, everolimus, for example.

Corticosteroid family of anti-inflammatory or anti-pruitic agents may include desonide, hydrocortisone, cortisone, clocortolone, clobetasol, desoximetasone, dexamethasone, fluocinolone, fluocinonide, prednisolone, diflorasone, betamethasone, triamcinolone, and derivatives thereof, for example. Non-steroid family of anti-inflammatory agents may include ibuprofen, diclofenac, naproxen, melcoxicam, piroxicam, and methyl salicylate, for example.

Proteins and enzymes may include collagenases, hyaluronidases, bromelain, papain, trypsin, for example.

Hair growth agents may include minoxidil, finasteride, spironolactone, for example. Active agents for ophthalmic diseases may include moxifloxacin, atropine, travoprost, olopatadine, natamycin, nepafenac, tropicamide, apraclonidine, bimatoprost, ketorolac, nedocromil, levobunolo, epinastine, ofloxacine, for example.

Active agents for dermatological diseases may include 5-fluorouracil, Azelaic acid, ivermectin, bromonidine, calcipotriene, retapamulin, salicylic acid, ingenol mebutate, for example.

Active agents, such as epidermal growth factor, transforming growth factor-α, transforming growth factor-β, heptocyte growth factor, vascular endothelial growth factor, platelet derived growth factor, fibroblast growth factor, keratinocyte growth factor, may be used for promoting wound healing.

Suitable combinations of the pharmacologically active agents may be used in the compositions of the present embodiment as long as such combinations offer pharmacological advantages for treating a medical condition. Additional examples of pharmacologically active agents include those compounds which are listed in the "*Therapeutic Category and Biological Activity Index*" of the Merck Index (15th edition, 2013), the entire contents of which are thereby incorporated by reference.

Examples of the cosmetically active agents include vitamins, such as vitamin B, vitamin C, tocopherols (vitamin E), tocopherol derivatives, tocotrienols, vitamin D, K and derivatives thereof, and suitable combinations thereof, for example.

Antioxidants may include cysteine, lipoic acid, melatonin, glutathione and derivatives thereof, and suitable combinations thereof, for example.

Moisturizing compounds may include glycerin, urea, methylurea, ethylurea, allantoin, lactates, sugars, methyl glucose ethers, sodium pyrrolidone carboxylic acid, sodium hyaluronate, panthenol, hyaluronic acid, α- and β-hydroxyl acids, such as glycolic acid, lactic acid, mandelic acid, or salicylic acid, or combinations of the suitable moisturizing compounds, for example.

The compositions may further comprise a penetration enhancer, such as tissue penetration enhancers, to enhance release and delivery of the active compound into tissues, such as, for example, skin, ocular, nasal. For these compositions, they might comprise both release enhancing agents of the present embodiment and tissue penetration enhancers. The tissue penetration enhancers may then enhance tissue absorption and penetration of the released active agent. The tissue penetration enhancers might be either in suspended solid or solubilized form in the compositions of the present embodiment.

Tissue penetration enhancers, such as suitable volatile organic solvents, include aliphatic, cycloaliphatic and/or aromatic-aliphatic alcohols, each of which is monohydric or polyhydric, alcohol/water mixtures, saturated and/or unsaturated fatty alcohols which each contains from about 8 to about 18 carbon atoms, saturated and/or unsaturated fatty acids which each contains from about 8 to about 18 carbon atoms and/or esters thereof and the like and mixtures thereof. Useful alcohols are those having from 1 to about 20 carbon atoms, e.g., ethanol, isopropyl alcohol, 1-butanol, 1-octanol, etc.

While not being bound to any particular theory, there are two theories supporting the use of alcohol as skin penetration enhancer. First, the alcohol evaporates fast and concentrates the drug in the residual formulation that remains on the skin. It is believed that some thermodynamic activity will drive the drug into the stratum corneum. Second, the alcohol alters the physical integrity of the stratum corneum barrier resulting in an increase in the ability of the drug to penetrate the skin. Commercially, denatured alcohol such as SDA 40 is often used in place of Alcohol USP (ethanol), and it may be used here also.

Tissue penetration enhancers, such as suitable amides for use as nonvolatile organic solvents may include N,N-dimethyl acetamide (DMA) N,N-diethyl toluamide, N,N-dimethyl formamide, N,N-dimethyl octamide, N,N-dimethyl decamide, and the like; pyrrolidone derivatives such as N-alkylpyrrolidones (e.g., N-methyl-2-pyrrolidones), vinyl pyrrolidone, 2-pyrrolidone, 2-pyrrolidone-5-carboxylic acid, N-(2-hydroxyethyl)-2-pyrrolidone or fatty acid esters thereof, 1-lauryl-4-methoxycarbonyl-2-pyrrolidone, N-tallow-alkylpyrrolidones, and the like and mixtures thereof.

Tissue penetration enhancers, such as polyol ethers for use herein can be C2-C30 polyol ethers containing from 2 to about 10 hydroxyl groups. Representative of the polyol ethers are glycol ethers which include, by way of example and without limitation, ethylene glycol monomethyl ether, ethylene glycol monoethyl ether, ethylene glycol monobutyl ether, ethylene glycol monopropyl ether, ethylene glycol monophenyl ether, ethylene glycol monohexyl ether, diethylene glycol monoethyl ether, diethylene glycol monomethyl ether, triethylene glycol monomethyl ether, triethylene glycol monoethyl ether, ethylene glycol monopropyl ether, ethylene glycol monobutyl ether, diethylene glycol monobutyl ether, triethylene glycol monobutyl ether, ethylene glycol monohexyl ether, diethyl glycol monohexyl ether, ethylene glycol phenyl ether, polyethylene glycol, polyethylene glycol dodecyl ether, diethylene glycol monoethyl ether, polyethylene glycol-8-glyceryl caprylate and the like and mixtures thereof.

Tissue penetration enhancers, such as diethylene glycol monoethyl ether, commercially available as Transcutol® (available from Gattefosse of St Priest Mi-Plaine, France), is a preferred polyol ether. Transcutol® can solubilize hydrophobic materials. The increased drug flux across the stratum corneum is explained by the diffusion of Transcutol® into it, thereby changing the ability of the drug to penetrate the intercellular space. It is believed that the primary role of Transcutol® is the modification of the thermodynamic activity of the drug. By direct action on its solubility, Transcutol® favors the passage of larger quantities of the drug into the stratum corneum allowing a greater solubilization in the aqueous domains of the tissue. Currently, there are various clinical studies conducted in the U.S. using Transcutol® in topical products (Phase I, II and III clinical trials).

Tissue penetration enhancers, such as polyols for use herein can be C2-C30 polyols containing from 2 to about 10 hydroxyl groups. Suitable polyols according to the present invention include, but are not limited to, propylene glycol, butylene glycol, hexylene glycol, 1,2-hexanediol, 1,2-heptanediol, propylene glycol monocaprylate and mixtures thereof.

In one embodiment, the skin penetration enhancers for use in the compositions may be the amides such as the foregoing pyrrolidones and will include one or more solvents that are pharmaceutically acceptable for application to skin or exposed tissue of a non-human. Suitable solvents include, but are not limited to, C1-C4 alcohols, C1-C4 alkylene glycols, C1-C4 polyalcohols, C1-C4 polyalkylene glycols, sorbates, polysorbates, benzyl alcohol, triglycerides, and water. Specific examples of suitable components for the solvent mixture include propylene glycol, glycerin, ethanol, isopropyl alcohol and the like. Specifically, propylene glycol, glycerin, isopropyl alcohol, ethanol, and the like, are recognized in the art as safe for topical application to non-human skin and/or exposed tissue.

For example, propylene glycol can serve as a moisturizer and can produce a pleasant emollient feel when applied to the skin. Furthermore, propylene glycol also has the added advantage of being a mild germicide. However, in excessive concentrations the germicidal properties can potentially irritate sensitive skin.

The composition may further include auxiliary agents. Auxiliary agents may include silicone oils, mineral oils, preservatives, anti-oxidants, chelating agents, coloring agents, for example.

In one embodiment, a topical composition may comprise (a) a therapeutically effective amount of an active agent; (b) a petrolatum ointment base; (c) C11-C40 alcohols or acids, or combinations thereof; and (d) substantially soluble polymer in the petrolatum ointment base. A combination of alcohols or acids with the polymer may enhance a release of the active agent.

In another embodiment, a process for preparing a composition may be carried out by steps of (a) dissolving or suspending a therapeutically effective amount of an active agent in an ointment base; (b) mixing C11-C40 alcohols or C11-C40 acids, or combinations thereof; and (c) mixing a polymer wherein the polymer is substantially soluble. In further embodiment, the process for preparing a composition may further be carried out by suspending an active agent in an ointment base. The polymer may be a copolymer, comprising a vinyl amide monomer and an olefin. The vinyl amide may be vinyl pyrrolidone. The olefin comprises α-olefin having at least 11 carbon atoms.

In one embodiment, a combination of the polymer and a fatty acid or fatty alcohol or their combinations are mixed with petrolatum. Upon heating the mixture to a temperature of about 40° C. or higher, the mixture is melt and solubilized. Then, the active agents may be added to the solubilized mixture as suspended solids.

In another embodiment, the active agents may be solubilized in another solvent or solvent mixture. Then, the solubilized active agents may then be added to the compositions comprising a combination of the said polymer and terminally fatty acid or fatty alcohol or their combinations.

In one embodiment, an ointment base, such as petrolatum, is a semi-solid mixture of hydrocarbons, typically having carbon numbers of 25 or higher. The hydrocarbons are believed to be densely and orderly packed. The dense and orderly packing of hydrocarbons is thought to be responsible for high viscosity and hydrophobicity of petrolatum. It is hypothesized that loosening and disruption of the orderly and dense packing might lead to increase in release of the active agents. It is unexpected discovered that a combination of a polymer that is soluble in petrolatum and a fatty acid or alcohol could lead to loosening and disruption of dense and orderly packing of hydrocarbons, resulting in enhanced release of the active agents.

Hydrophobicity of fatty alcohol or acid also increases as the hydrocarbon chain length increases. In other words, fatty alcohol or acid of longer chain is more soluble in the ointment base than shorter chain. Thus, longer chain terminally functionalized fatty alcohol or acid may be preferred than the shorter chain one.

The active agents have different chemical structures and properties. A suitable combination of a copolymer and fatty alcohol or acid that is best suited for a particular active agent is typically determined by conducting in vitro release test experiments.

In vitro release test using a synthetic membrane is a common method to study release of a pharmaceutically active compound from semi-solid dosage forms (including ointments, creams, lotions, gels, pastes, foams, and other viscous liquids). It is one of important performance tests to evaluate and characterize a semi-solid dosage form. The release test is typically conducted in a diffusion cell apparatus. A diffusion cell consists of a donor and receptor chamber separated by a synthetic membrane. The ointments to be tested are dosed into the donor chamber in infinite dose application. The receptor chamber is filled with a receptor fluid to solubilize the released active agent. Concentrations of the released active agent in the receptor fluid can then be analyzed to obtain the release rate.

All percentages referred to in this specification are percentages by weight of the total composition unless otherwise indicated.

The following examples are included for purposes of illustrating the technology covered by this disclosure. They are not intended to limit the scope of the claimed invention in any manner. One skilled in the art will understand that there are alternatives to these specific embodiments that are not completely described by these examples.

Example 1

Assay Method—In Vitro Release Testing (IVRT)

Release of the active agents from the petrolatum based compositions was evaluated in an in vitro model of diffusion cells using a synthetic membrane model. In vitro release testing (IVRT) of the active agent into a receptor medium was measured over 16 hours using a UV-VIS spectrometer.

IVRT Test Conditions:
Test temperature: 32° C.
Test period: 16 hours.
Receptor medium: 1-Octanol/ethyl alcohol/water at (50/47.5/2.5, volume ratio).
Membrane: Polypropylene (0.45 micron).
Diffusion cell parameters: diameter of the membrane diffusion area is about 11 mm. Volume of the receptor chamber is about 12 milliliter. Dosing level: infinite dose is at about 3.0 ml of the compositions according to the present embodiment.

Diffusion cell consists of a donor and receptor chamber separated by a synthetic membrane. The membrane is generally selected through conducting membrane binding experiments. Any membrane that shows substantially no binding to the active agent might be used in the IVRT experiments. The receptor chamber was filled with a receptor medium with suitable solubility of the released active agent. The receptor medium was mixed with a mixing mechanism, such as, e.g., magnetic stirring bar, orbit shaker, and maintained at 32° C. with a heating mechanism, such as, e.g., dry heat block, circulating water bath. At end of the test period, samples were taken from the receptor medium and analyzed by a UV-VIS spectrometer or other suitable analytical techniques, such as, for example, HPLC, LC-MS. IVRT may also be performed at other suitable temperatures, such as, for example, 37° C.

Release enhancing ratio (RER) can be calculated from the following equation:

RER=(Amount of the released active agent from a petrolatum based composition of the present embodiment)/(Amount of the released active agent from a petrolatum-only composition).

This ratio is a measure of ability of a release enhancing agent to enhance release of the active agent from a composition.

Example 2

Preparation of the Compositions

This example demonstrates general procedure to prepare the compositions according to the present embodiments. Petrolatum, the release enhancing agents, and other agents, if needed, were combined. The mixture was heated to about 40-80° C. while mixing. The active agent(s) was added to the mixture either in suspended solid or solubilized form while heating while mixing. The mixture was mixed until uniform. Then, the mixture was cooled to room temperature while mixing to yield the topical compositions.

| Compositions containing active ingredients | |
|---|---|
| Ingredients | Percentage (%) |
| Active agent(s) | q.s |
| Release enhancing agents | q.s |
| Other ingredients | q.s |
| Petrolatum | >=50 |

Example 3

Release of Nile Red in Petrolatum Based Compositions
Nile Red (0.1%) was selected as a model active agent. Ganex V220-F is selected as the copolymer. It is a copolymer of vinylpyrrolidone and 1-eicosene. In this example, Nile Red was dispersed into petrolatum based compositions as solids.

The IVRT experiment was conducted for 16 hours at four replicates (N=4) per composition. After the experiment, samples were collected from the receptor chamber and analyzed by UV-VIS spectrometer. All experiments were conducted in the same batch to minimize any interday variation.

| Compositions | Concentration in receptor medium (μg/ml) | RER ratio |
|---|---|---|
| 2% Ganex V-220F, 97.9% petrolatum (Comparative) | 3.18 ± 0.54 | 4.13 |
| 5% 1-Docosanol, 94.9% petrolatum (Comparative) | 3.31 ± 0.16 | 4.30 |
| 2% Ganex V-220F, 5% 1-docosanol, 92.9% petrolatum (Present embodiment) | 12.75 ± 0.56 | 16.56 |
| 99.9% Petrolatum (Comparative) | 0.77 ± 0.41 | 1.00 |

The RER value from the composition comprising a combination of Ganex V-220F and a fatty alcohol, 1-docosanol, was found to be 16.56. The RER value from the composition comprising only Ganex V-220F was 4.13. And the RER value from the composition comprising only 1-docosanol was 4.30. The RER value from the composition of the present embodiment is significantly higher than sum (4.13+4.30=8.43) of the RER value from compositions comprising either the copolymer only, or the fatty alcohol only. This indicates a synergistic effect of release enhancement from the composition of the present embodiment.

Example 4

Release of Nile Red as a Function of Concentrations
Nile Red (0.1%) was selected as a model active agent. Ganex V220-F is a copolymer of vinylpyrrolidone and 1-eicosene. In this example, Nile Red was dispersed into petrolatum-based compositions as solids.

The IVRT experiment was conducted for 16 hours at four replicates (N=4) per composition. After the experiment, samples were collected from the receptor chamber and analyzed by UV-VIS spectrometer. All experiments were conducted in the same batch to minimize any interday variation.

| Compositions | Concentration in receptor medium (μg/ml) | RER ratio |
|---|---|---|
| 2% Ganex V-220F, 5% 1-dococanol, 92.9% petrolatum | 14.72 ± 1.01 | 13.38 |
| 2% Ganex V-220F, 2.5% 1-docosanol, 95.4% petrolatum | 8.79 ± 0.78 | 8.00 |
| 1% Ganex V-220F, 5% 1-docosanol, 93.9% petrolatum | 12.95 ± 0.93 | 11.77 |
| 99.9% Petrolatum | 1.10 ± 0.07 | 1.00 |

When concentration of Ganex V-220F was cut in half, release of Nile Red was basically not affected. However, when concentration of 1-docosanol was cut in half, release of Nile Red was significantly affected (dropped by about 40%). The example suggests that the copolymer at 1% concentration would be sufficient for the release enhancement. For the fatty alcohol, a higher concentration is needed to achieve the synergistic effect. The example also demonstrates that the release enhancement effect is concentration-dependent.

Example 5

Release of Nile Red as a Function of Chain Length in Fatty Alcohol

Nile Red (0.1%) was selected as a model active agent. Ganex V220-F is a copolymer of vinylpyrrolidone and 1-eicosene. In this example, Nile Red was dispersed into petrolatum-based compositions as solids.

The IVRT experiment was conducted for 16 hours at four replicates (N=4) per composition. After the experiment, samples were collected from the receptor chamber and analyzed by UV-VIS spectrometer. All experiments were conducted in the same batch to minimize any interday variation.

| Compositions | Concentration in receptor medium (µg/ml) | RER ratio |
|---|---|---|
| 2% Ganex V-220F, 5% Stearyl alcohol, 92.9% petrolatum | 7.10 ± 1.20 | 6.70 |
| 2% Ganex V-220F, 5% 1-nonadecanol, 92.9% petrolatum | 9.42 ± 0.37 | 8.89 |
| 2% Ganex V-220F, 5% 1-eicosanol, 92.9% petrolatum | 10.42 ± 0.34 | 9.83 |
| 2% Ganex V-220F, 5% 1-tetracosanol, 92.9% petrolatum | 16.74 ± 0.34 | 15.79 |
| 99.9% Petrolatum | 1.06 ± 0.11 | 1.00 |

This example demonstrates that as chain length of the fatty alcohol increases, release of Nile Red increases.

Example 6

Release of Nile Red as Suspended Solid and Solubilized Form

Nile Red (0.1%) was selected as a model active agent. Ganex V220-F is a copolymer of vinylpyrrolidone and 1-eicosene. In this example, Nile Red was solubilized in dimethyl isosorbide. Rest of the ingredients was combined and solubilized in petrolatum. Nile Red solution was then added to the mixture.

The IVRT experiment was conducted for 16 hours at four replicates (N=4) per composition. After the experiment, samples were collected from the receptor chamber and analyzed by UV-VIS spectrometer. All experiments were conducted in the same batch to minimize any interday variation.

| Compositions | Concentration in receptor medium (µg/ml) | RER ratio |
|---|---|---|
| 2% Ganex V-220F, 5% 1-docosanol, 92.9% petrolatum | 12.96 ± 0.52 | 12.58 |
| 0.1% Nile Red solubilized in 10% dimethyl isosorbide, 2% Ganex V-220F, 5% 1-docosanol, 82.9% petrolatum | 12.13 ± 2.92 | 11.78 |
| 99.9% Petrolatum | 1.03 ± 0.14 | 1.00 |

This example demonstrates that the release enhancement effect was observed when Nile Red was added either as in suspended solid or solution form.

Example 7

Release of Fenofibrate from Petrolatum Based Formulations

Fenofibrate (1.0%) was selected as a model active agent. Fenofibrate is used for treatment of hypercholesterolemia and dyslipidemia. Ganex V220-F is a copolymer of vinylpyrrolidone and 1-eicosene. In this example, fenofibrate was dispersed into the compositions as solids.

The IVRT experiment was conducted for 16 hours at four replicates (N=4) per composition. After the experiment, samples were collected from the receptor chamber and analyzed by UV-VIS spectrometer. All experiments were conducted in the same batch to minimize any interday variation.

| Compositions | Concentration in receptor medium (µg/ml) | RER ratio |
|---|---|---|
| 2% Ganex V-220F, 5% 1-docosanol, 92% petrolatum | 184.30 ± 1.10 | 44.95 |
| 2% Ganex V-220F, 5% Behenic acid, 92% petrolatum | 217.10 ± 8.00 | 52.95 |
| 99% Petrolatum | 4.10 ± 0.10 | 1.00 |

This example demonstrates that a combination of a fatty acid (behenic acid) or alcohol (1-docosanol) and Ganex V-220F synergistically enhances release of fenofibrate.

Example 8

Release of an Antibiotic from Petrolatum Based Compositions

A composition of the present disclosure is suitable to enhance release of a pharmaceutically active agent from the composition.

| Ointment Dosage Form | |
|---|---|
| Ingredients | Percentage (%) |
| Mupirocin | 2 |
| 1-Docosanol | 5 |
| Ganex V-220F | 1 |
| Petrolatum | 92 |

Release of an antibiotic, such as mupirocin, is enhanced in the presence of a fatty alcohol, 1-docosanol, and a copolymer, Ganex V-220F.

Example 9

Release of an Antifungal and Corticosteriod from Petrolatum Based Compositions

A petrolatum-based composition of the present disclosure is suitable to enhance release of two pharmaceutically active agents from the composition.

Ointment Dosage Form

| Ingredients | Percentage (%) |
|---|---|
| Nystatin* | * |
| Triamcinolone acetonide | 0.1 |
| Behenic acid | 5 |
| Ganex V-220F | 1 |
| Petrolatum | 93.9 |

*About 100,000 international units per gram of the composition.

Release of antifungal, such as nystatin, and a corticosteroid, triamcinolone acetonide, is enhanced in the presence of a fatty acid, behenic acid, and a copolymer, Ganex V-220F.

Example 10

Release of a Wound Healing Agent from Petrolatum Based Compositions

A petrolatum-based composition of the present disclosure is suitable to enhance release of a pharmaceutically active agent from the composition.

Ointment Dosage Form

| Ingredients | Percentage (%) |
|---|---|
| Collagenase* | * |
| 1-Docosanol | 5 |
| Ganex V-220F | 1 |
| Petrolatum | 94 |

*About 250 collagenase units per gram of petrolatum based composition.

Collagenase is an enzyme that removes dead tissue from wounds to help wound healing. Release of active agent, such as collagenase, is enhanced in the presence of a fatty alcohol, 1-docosanol, and a copolymer, Ganex V-220F.

Example 11

Release and Skin Penetration Enhancement of an Active Agent from Petrolatum Based Compositions A petrolatum-based composition of the present disclosure is suitable to enhance release and skin penetration of a pharmaceutically active agent from the composition.

Delivery of an active agent into animal or human tissues, such as, for example, skin, ocular, or nasal tissue, may be achieved by application of a topical composition to the tissue surface. It consists of two processes. Take skin tissue as an example. The first process is release and diffusion of the active agent from the applied composition to skin surface. The second process is absorption of the released active agent into various skin layers (e.g., stratum corneum, epidermis, and dermis) and penetration through these layers into subcutaneous fat layer and systemic circulation.

The present embodiment teaches enhancement of release of an active agent from a topical ointment composition. In the presence of a skin penetration enhancer or combinations of skin penetration enhancers, skin penetration of the released active ingredient could be enhanced.

Ointment Dosage Form

| Ingredients | Percentage (%) |
|---|---|
| Betamethasone dipropionate | 0.064 |
| 1-Docosanol | 5 |
| Ganex V-220F | 1 |
| Azone* | 2 |
| Petrolatum | 91.936 |

*1-dodecylazacycloheptan-2-one.

When the composition is applied to skin surface, the combination of Ganex V-220F and 1-docosanol enhances release of betamethasone dipropionate from the composition. Azone is a skin penetration enhancer. Addition of Azone in the ointment could enhance skin absorption and penetration of the released betamethasone dipropionate.

Having described the subject matter of the present disclosure in detail and by reference to specific embodiments thereof, it is noted that the various details disclosed herein should not be taken to imply that these details relate to elements that are essential components of the various embodiments described herein.

The claims appended hereto should be taken as the sole representation of the breadth of the present disclosure and the corresponding scope of the various embodiments described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present disclosure, it is noted that this term is introduced in the claims as an open-ended transitional phrase that is used to introduce a recitation of a series of characteristics of the structure and should be interpreted in like manner as the more commonly used open-ended preamble term "comprising."

While the invention has been described with respect to a limited number of embodiments, those skilled in the art, having benefit of this disclosure, will appreciate that other embodiments can be devised that do not depart from the scope of the invention as disclosed herein. Accordingly, the scope of the invention should be limited only by the attached claims.

The invention claimed is:

1. A topical composition, comprising:
   an ointment base in an amount of at least about 50% of the topical composition by weight;
   C11-C40 alcohols or C11-C40 acids, or combinations thereof; and
   a substantially soluble polymer in the ointment base.

2. The topical composition of claim 1, further comprising an active agent.

3. The topical composition of claim 2, wherein the active agent is selected from the group consisting of analgesic agents, anesthetic agents, anti-microbial agents, anti-viral agents, cardio, estrogens, retinoids, immunosuppressive agents, corticosteroids, non-steroidal anti-inflammatory drugs (NSAIDs), proteins, enzymes, hair-growth agents, ophthalmic agents, dermatological agents, cosmetic agents, moisturizing agents, urea, allantoin, antifungal agents, antibacterial agents, and wound-healing agents.

4. The topical composition of claim 1, wherein the alcohols or acids have from C16 to C40.

5. The topical composition of claim 1, wherein the alcohols or acids have a concentration of from about 0.1% to about 20% by weight.

6. The topical composition of claim 1, wherein the polymer comprises a copolymer.

7. The topical composition of claim 6, wherein the copolymer comprises a vinyl amide monomer and an olefin.

8. The topical composition of claim 7, wherein the vinyl amide is vinyl pyrrolidone.

9. The topical composition of claim 7, wherein the olefin comprises an α-olefin having at least 11 carbon atoms.

10. The topical composition of claim 1, wherein the polymer has a concentration of from about 0.1% to about 20% by weight.

11. The topical composition of claim 1 further comprising a tissue penetration enhancer.

12. A topical composition, comprising:
(a) a therapeutically effective amount of an active agent;
(b) a petrolatum ointment base;
(c) C11-C40 alcohols or C11-C40 acids, or combinations thereof; and
(d) a substantially soluble polymer in the petrolatum ointment base, wherein a combination of alcohols or acids with the polymer enhances a release of the active agent.

13. The topical composition of claim 12, wherein the alcohols or acids have from about 16 to 40 carbon atoms.

14. The topical composition of claim 12, wherein the alcohols or acids have a concentration of from about 0.1% to about 20% by weight.

15. The topical composition of claim 12, wherein the polymer comprises a copolymer.

16. The topical composition of claim 15, wherein the copolymer comprises a vinyl amide monomer and an olefin.

17. The topical composition of claim 16, wherein the vinyl amide is vinyl pyrrolidone.

18. The topical composition of claim 16, wherein the olefin comprises an α-olefin having at least 11 carbon atoms.

19. The topical composition of claim 16, wherein the ointment composition further comprises a tissue penetration enhancer.

20. A process for preparing an ointment composition comprising:
(a) dissolving or suspending a therapeutically effective amount of an active agent in an ointment base;
(b) mixing C11-C40 alcohols or C11-C40 acids, or combinations thereof; and
(c) mixing a polymer wherein the polymer is substantially soluble in the ointment base.

21. The process of claim 20, wherein the alcohols or acids have a concentration of from about 0.1% to about 20% by weight.

22. The process of claim 20, wherein the polymer has a concentration of from about 0.1% to about 20% by weight, wherein the polymer comprises a copolymer.

23. The process of claim 20, wherein the copolymer comprises a vinyl amide monomer and an olefin, wherein the vinyl amide is vinyl pyrrolidone, the olefin comprises an α-olefin having at least 11 carbon atoms.

* * * * *